US009651503B2

(12) United States Patent
Bueno et al.

(10) Patent No.: US 9,651,503 B2
(45) Date of Patent: May 16, 2017

(54) SYSTEM AND METHOD FOR SURFACE INSPECTION

(71) Applicant: GENERAL ELECTRIC COMPANY, Schenectady, NY (US)

(72) Inventors: Manuel Kenneth Bueno, Syracuse, NY (US); Robert Martin Roney, Jr., Schoharie, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/665,748

(22) Filed: Mar. 23, 2015

(65) Prior Publication Data

US 2016/0069820 A1 Mar. 10, 2016

Related U.S. Application Data

(60) Provisional application No. 62/046,692, filed on Sep. 5, 2014.

(51) Int. Cl.
*G01B 11/24* (2006.01)
*G01N 21/954* (2006.01)
*G01S 17/89* (2006.01)
*G01N 21/88* (2006.01)
*G01S 17/88* (2006.01)
*G01S 7/481* (2006.01)

(52) U.S. Cl.
CPC ....... *G01N 21/954* (2013.01); *G01N 21/8851* (2013.01); *G01S 7/4815* (2013.01); *G01S 7/4817* (2013.01); *G01S 7/4818* (2013.01); *G01S 17/88* (2013.01); *G01S 17/89* (2013.01); *G01N 2021/9544* (2013.01); *G01N 2021/9548* (2013.01); *G01N 2201/06113* (2013.01); *G01N 2201/104* (2013.01)

(58) Field of Classification Search
CPC .......... G01V 1/00; E02B 3/00; G01N 21/954; G01N 21/8851; G01N 2201/104; G01N 2021/9548; G01N 2201/06113; G01S 17/89
USPC .... 356/607, 613–614, 226; 367/16, 20, 141, 367/153
See application file for complete search history.

(56) References Cited

U.S. PATENT DOCUMENTS

| 6,959,603 | B2 | 11/2005 | Knight et al. |
| 7,552,631 | B2* | 6/2009 | Harthorn ................. E21B 17/01 73/152.57 |
| 8,842,297 | B2* | 9/2014 | Storksen ............ G01B 11/0616 250/559.22 |
| 2004/0114793 | A1* | 6/2004 | Bondurant ........... G01N 21/954 382/141 |
| 2008/0105067 | A1* | 5/2008 | Frey ...................... G01B 11/24 73/865.8 |

(Continued)

*Primary Examiner* — Tarifur Chowdhury
*Assistant Examiner* — Isiaka Akanbi
(74) *Attorney, Agent, or Firm* — Fletcher Yoder, P.C.

(57) ABSTRACT

A system includes a vessel floating on a body of water. The system also includes at least one conduit extending from the vessel to below the body of water. The system also includes a scanning device disposed within the at least one conduit. The scanning device includes at least one two-dimensional (2D) line scanner and a rotary encoder coupled to the at least one 2D line scanner. The scanning device is configured to generate three-dimensional (3D) image data of a surface of the at least one conduit or at least one component disposed within the at least one conduit.

14 Claims, 7 Drawing Sheets

(56) References Cited

U.S. PATENT DOCUMENTS

2012/0069172 A1* 3/2012 Hudritsch ............ G01N 21/954
  348/84

* cited by examiner

SYSTEM AND METHOD FOR SURFACE INSPECTION

CROSS REFERENCE TO RELATED APPLICATION

This application claims priority from and the benefit of U.S. Provisional Application Ser. No. 62/046,692, entitled "SYSTEM AND METHOD FOR SURFACE INSPECTION", filed Sep. 5, 2014, which is hereby incorporated by reference in its entirety.

BACKGROUND

The subject matter disclosed herein relates to non-destructive inspection of pipes, and more specifically to a system and method for inspection of interior surface of pipes using laser line scanners.

During hydrocarbon extraction, a drilling riser may be utilized for offshore drilling, extending from a drilling rig on a drilling vessel down to a subsea wellhead. The drilling riser may include multiple riser sections (e.g., pipes) that are joined together with connectors or by welding. During use, a drill pipe, a casing, and other well tools may be lowered through the drilling riser, and drilling mud may return up to the drilling vessel in the drilling riser. As such, the drill riser may be periodically inspected for analyzing structural integrity (e.g., for corrosion of interior, degrading of welding, or loosening of connectors).

However, inspection of the drilling riser is often done by pulling the drilling riser up from undersea, disconnecting riser sections, and transporting the riser sections to an onshore facility. It is time consuming and expensive to dissemble, transport, inspect, and reassemble the riser sections. During this time, unless a spare drilling riser can be used, the drilling rig would not be able to operate. Accordingly, there is a need for a non-destructive inspection device for inspecting (e.g., interior surface of) a deployed drilling riser.

BRIEF DESCRIPTION

Certain embodiments commensurate in scope with the present disclosure are summarized below. These embodiments are not intended to limit the scope of the claim, but rather these embodiments are intended only to provide a brief summary of the present disclosure. Indeed, embodiments of the present disclosure may encompass a variety of forms that may be similar to or different from the embodiments set forth below.

In a first embodiment, a system includes a vessel floating on a body of water. The system also includes at least one conduit extending from the vessel to the body of water. The system also includes a scanning device disposed within the at least one conduit. The scanning device includes at least one two-dimensional (2D) line scanner and a rotary encoder coupled to the at least one 2D line scanner. The scanning device is configured to generate three-dimensional (3D) image data of a surface of the at least one conduit or at least one component disposed within the at least one conduit.

In a second embodiment, a system includes a scanning device configured to be disposed within a conduit. The scanning device includes at least one two-dimensional (2D) line scanner and a rotary encoder coupled to the at least one 2D line scanner. The scanning device is configured to generate two-dimensional (2D) image data of a first surface of the conduit, a second surface of a component disposed within the conduit, or a third surface of an object disposed above the conduit. The system also includes a controller coupled to the scanning device and configured to acquire the 2D image data from the scanning device and to generate three-dimensional (3D) image data from at least the acquired 2D image data.

In a third embodiment, a method includes disposing a scanning device within a conduit. The scanning device includes at least one two-dimensional (2D) line scanner and a rotary encoder coupled to the at least one 2D line scanner. The method also includes acquiring two-dimensional (2D) image data of a first surface of the conduit, a second surface of a component within the conduit, or a third surface of an object disposed above the conduit using the scanning device. The method also includes generating three-dimensional (3D) image data from at least the acquired 2D image data.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
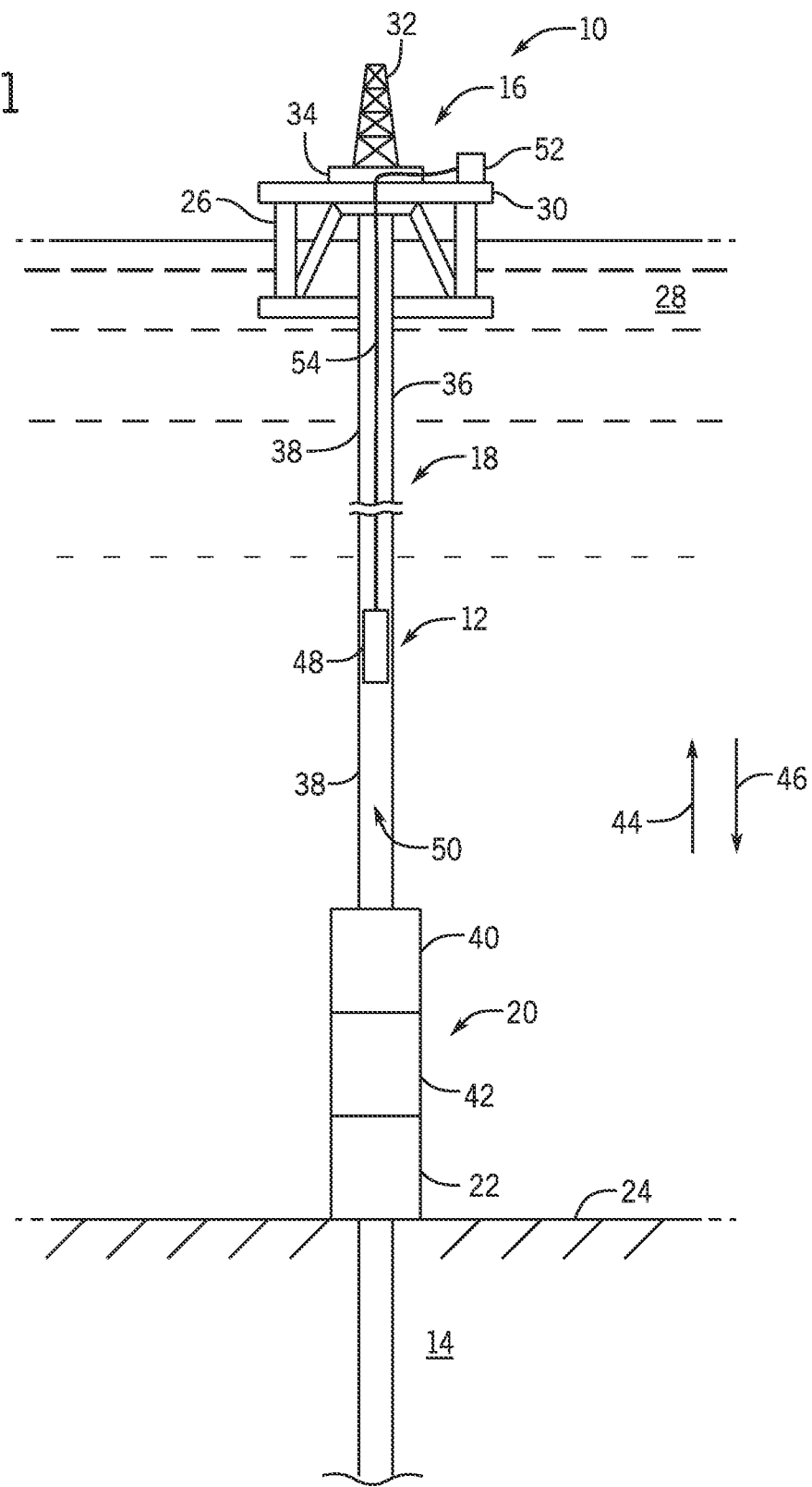
FIG. 1 is a schematic view of an embodiment of a hydrocarbon extraction system with an inspection system in accordance with the present the disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

The present disclosure provides an inspection system for non-destructive inspection of suitable tubular structures of a hydrocarbon extraction system. For example, the tubular structures may include drilling riser pipes. The inspection system, in accordance with the present disclosure, may be deployed or positioned within the drilling riser pipes for inspecting the interior surfaces of the drilling riser pipes without disassembling, transporting, or reassembling components of the drilling riser pipes, thus, may be deployed within drilling riser pipes when the drilling riser pipes are set up for offshore drilling. The inspection system may also be deployed or positioned within other components of the hydrocarbon extraction system, such as a blowout preventer (BOP), or may be deployed onto or proximate to any wetted surfaces of various components of the hydrocarbon extraction system.

Embodiments of inspection system may include a scanning device, a controller, and one or more cables coupling the scanning device and the controller. The scanning device may include one or more (e.g., 1 to 20, or above) two-dimensional (2D) line scanners, each configured to line scan a portion of a circumference of the interior surface of the drilling riser pipe. In certain embodiments, the scanning device may also scan surfaces of objects above the water surface and/or outside of conduits (e.g., on the deck of the drilling rig). In addition, the scanning device may also scan an interior surface of a conduit or component within the conduit utilized in land-based or onshore drilling operations. The scanning device may also include a motor configured to drive the one or more line scanners to rotate, and a rotary encoder configured to monitor angular positions of the one or more line scanners. The rotary encoder may transmit data related to the angular positions of the one or more line scanners to the controller. The controller may then control the motor to drive the scanning device to rotate, for example, one or more rotational sweeps, such that the whole circumference of the interior surface of the drilling riser pipe may be line scanned to generate a 2D image. The one or more cable lines may be controlled by the controller to move the scanning device to one or more other depths. Similarly, one or more 2D images may be generated by line scanning the interior surface of the drilling riser pipe at the one or more other depths. The acquired multiple 2D images may then be transmitted to the controller via the one or more cables. The controller may generate a three-dimensional (3D) image of the interior surface of the drilling riser pipe based on the acquired multiple 2D images corresponding to the multiple depths and/or the data provided by the rotary encoder. The generated 3D image may be further processed or analyzed for determining structural integrity (e.g., for corrosions, or buildups of contaminates) of the interior surface of the drilling rise pipe.

With the foregoing in mind and turning now to the figures, a hydrocarbon extraction system 10 including an inspection system 12, in accordance with the present disclosure, is illustrated in FIG. 1. The hydrocarbon extraction system 10 facilitates extraction of a hydrocarbon resource, such as oil or natural gas, from a well 14. The hydrocarbon extraction system 10 includes a variety of equipment, including surface equipment 16, riser equipment 18, and stack equipment 20, for extracting the hydrocarbon resource from the well 14 via a wellhead 22. Connectors may facilitate coupling the various equipment packages (e.g., surface equipment 16, riser equipment 18, stack equipment 20, wellhead 22) of the hydrocarbon extraction system 10 to one another and/or various components within an equipment package to one another. In the illustrated embodiment, the hydrocarbon extraction system 10 is employed in an offshore drilling application for hydrocarbon extraction under the sea bottom 24, however, it should be noted that the hydrocarbon extraction system may be employed in a variety of other drilling or extraction applications, including onshore drilling applications.

The surface equipment 16 may include a variety of devices and systems, such as pumps, power supplies, cable and hose reels, control units, a diverter, a rotary table, and the like. For example, as illustrated, the surface equipment 16 may be part of or coupled to a floating vessel 26 floating on a body of water 28. The floating vessel 26 includes an operational platform 30 having a drilling rig 32. A spider 34 is located on the operational platform 30 and may provide support to a proximal end of the riser equipment 18.

The riser equipment 18 includes a conduit (e.g., drilling riser pipe) 36 that may include one or more riser pipe sections 38. The drilling riser pipe 36 extends between the floating vessel 26 and the sea bottom 24 via the wellhead 22. The riser equipment 18 may also include a variety of other components, such as pipe section joints, valves, control units, and sensors, among others. In some embodiments, the riser equipment 18 may include a lower marine riser package (LMRP) 40 at its distal end (e.g., closer to the sea bottom 24). The riser equipment 18 facilitates transfer of drilling equipments (e.g., drill pipes, casing, and other well tools) therewithin down to the sea bottom 24 and transmission of drilling fluid (or drilling mud) and/or the extracted resource to the surface equipment 16 from the well 14 via the wellhead 22.

The stack equipment 20 is coupled to the wellhead 22 proximate to the sea bottom 24 at its distal end, and to the riser equipment 18 (e.g., the LMRP 40) at its proximal end. The stack equipment 20 may also include a number of components, such as one or more blowout preventers (BOPS) 42, a subsea manifold, and/or production trees (e.g., completion or "Christmas" trees) for extracting the desired resource from the wellhead 22 and transmitting it to the surface equipment 16 via the riser equipment 18. The desired resource extracted from the wellhead 22 is transmitted to the surface equipment 16 generally in an upward direction 44. As utilized herein, a downward direction 46 is hereby defined as opposite the upward direction 44, such that the downward direction 46 is the general direction from the surface equipment 16 to the well 14.

The inspection system 12, in accordance with the present disclosure, may be employed within the hydrocarbon extraction system 10 for inspection of any suitable tubular structures thereof. As illustrated in FIG. 1, the inspection system 12 includes a scanning device 48 that may be disposed within a bore 50 of the drilling riser pipe 36. As discussed in greater detail below, the scanning device 48 may be manually or automatically deployed (e.g., via a wireline) within the bore 50 of the drilling riser pipe 36 to inspect the interior surface of the drilling riser pipe 36. It should be noted, however, that the scanning device 48 may be disposed within any suitable tubular structures of the hydrocarbon extraction system 10, including, but not limited to, other components of the riser equipment 18 (e.g., the LMRP 40), components of the stack equipment 20 (e.g., the one or more BOPs 42), and components of the wellhead 22. As also discussed in greater detail below, the inspection system 12 may also include a controller 52 coupled to the scanning device 48 for controlling operations of the scanning device, including movement control, position tracking, and data collection, transfer, and/or processing. The controller 52 may be disposed in the floating vessel 26 and be communicatively coupled (e.g., electronically) to the scanning device 48 via an umbilical cable 54.

Figure 2:
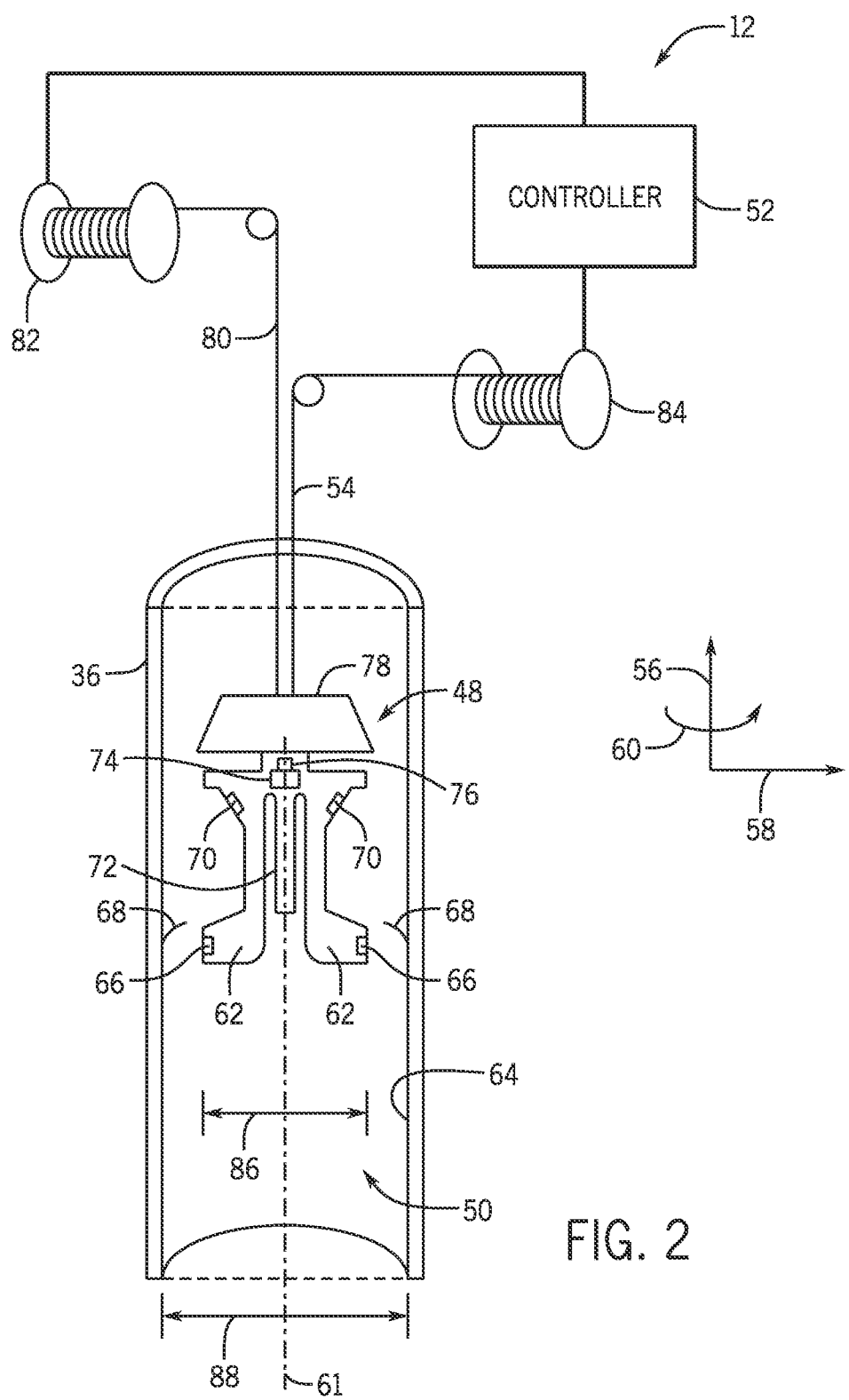
FIG. 2 is a schematic diagram of an embodiment of the inspection system of FIG. 1 disposed within a conduit (e.g., a riser pipe), in accordance with the present the disclosure.

FIG. 2 is a schematic diagram of the inspection system 12 of FIG. 1. The inspection system 12 includes the scanning device 48 that may be deployed within the bore 50 of the drilling riser pipe 36. The disclosed embodiments may be described with respect to an axial axis 56, a radial axis 58, and a circumferential axis 60. In addition, the scanning device 48 may have a longitudinal axis 61 substantially through the center of the scanning device 48. As illustrated, when the scanning device 48 is deployed within the bore 50 of the drilling riser pipe 36, the longitudinal axis 61 of the scanning device 48 is generally parallel to the axial axis 56 and runs generally through the center of the bore 50 of the drilling riser pipe 36. However, it should be noted that the scanning device 48 may be deployed in any suitable position within the bore 50 with respect to the drilling riser pipe 36.

As illustrated in FIG. 2, the scanning device 48 includes two two-dimensional (2D) line scanners 62 for inspection of the interior surface 64 (e.g., wall of the bore 50) of the drilling riser pipe 36. However, it should be noted that the scanning device 48 may include any number of the 2D line scanners 62, such as 1, 2, 3, 4, 5, 6, 7, 8, 9, 10, or more. The 2D line scanners 62 may be any suitable type of 2D line scanners, such as laser line scanners, configured to emit a beam of light to probe a surface (e.g., the interior surface 64 of the drilling riser pipe 36, or any wetted surface of various components of the hydrocarbon extraction system) by shining the beam of light on the surface and exploiting a camera to look for the location of the intersection line between the light beam and the surface. As such, protrusions (or obstacles) and cavities (or holes) of the surface in the intersection line between the light beam and the surface may have different locations in the field of view of the camera. Therefore, the image obtained from the camera may be used to determine the characteristics (e.g., profile) of the surface.

As illustrated, each of the line scanners 62 may include an emitter 66 (e.g., a laser emitter) configured to emit a beam of light traveling substantially perpendicular to the interior surface 64 (e.g., along the radial axis 58) of the drilling riser pipe 36. As discussed in greater detail below, the light beam intersects with the interior surface 64 by a substantially thin intersection line 68 extending along a portion of a circumference of the interior surface 64 (e.g., along the circumferential axis 60). Each of the line scanners 62 may also include a camera 70 configured to capture the respective intersection line 68 in the field of view of the camera 70. For example, the emitter 66 may emit a visible laser light with wavelength between approximately 400 nm and 760 nm, and the camera 70 may include imaging or sensing components configured to obtain images in the visible light range. As another example, the emitter 66 may emit an infrared (IR) laser light with wavelength above approximately 760 nm, and the camera 70 may include imaging or sensing components configured to obtain images in the IR light range. In addition, the emitter 66 may emit a continuous wave and/or a pulsed laser light with any suitable repetition pulse rate, and the camera 70 may obtain images continuously and/or with any suitable rate. In some embodiments, the emitter 66 may emit light at various different wavelengths and/or different repetition rate.

As illustrated, the two line scanners 62 are coupled to a shaft 72 disposed substantially along the longitudinal axis 61 of the scanning device and substantially symmetric to one another with respect to the shaft 72. A motor 74 is coupled to the shaft 72 and configured to drive the scanning device 48 to rotate with respect to the shaft (or the longitudinal axis 61). The motor 74 may be driven by any suitable power source either locally (e.g., a battery included in the scanning device 48) or remotely (e.g., via a power cable that is coupled to a remote power source, such as an electrical outlet, a battery, or a generator). As discussed below, the motor 74 may be communicatively coupled to the controller 52 configured to control operations of the motor 74.

The scanning device 48 also includes a rotary encoder 76, for example, coupled to the shaft 72, for determining or monitoring angular positions of the shaft 72. As the line scanners 62 are coupled to the shaft 72, the rotary encoder 76 may consequently determine or monitor angular positions of each of the line scanners 62 as they rotate (e.g., driven by the motor 74) with respect to the shaft 72 (or the longitudinal axis 61). The rotary encoder 76 may be any suitable type of rotary encoder, including an absolute and an incremental rotary encoder. The data related to the angular positions of the shaft and/or the line scanners 62 provided by the rotary encoder 76 may be transmitted to the controller 52. Based on the angular positions, the controller 52 may control the motor 74 to drive the scanning device 48 to rotate in any controlled manner. For example, the motor 74 may drive each of the 2D line scanners 62 to rotate with respect to the shaft 72 (or the longitudinal axis 61) any degree (e.g., between approximately 0 degree and 360 degrees) along the circumferential axis 60. In addition, the motor 74 may drive each of the 2D line scanners 62 to rotate continuously or in discrete steps. For example, each of the 2D line scanners 62 may rotate a certain degree along the circumferential axis 60 before line scanning a portion of a circumference of the interior surface 64 of the drilling riser pipe 36, and then continue to rotate the same or a different degree along the circumferential axis 60 to line scan another portion of the circumference of the interior surface 64, and so forth. As such, all of the circumference of the interior surface 64 of the drilling riser pipe 36 may be line scanned when the scanning device is deployed within the core 50 of the drilling riser pipe 36 at a specific depth along the axial axis 56. Similarly, when the scanning device is deployed within the core 50 at another depth along the axial axis 56, another circumference of the interior surface 64 may be line scanned. Consequently, a three-dimensional (3D) image or data of the interior surface 64 of the drilling riser pipe 36 may be obtained based at least on the obtained 2D images and/or the data provided by the rotary encoder 76. As discussed below, the motor 74 and the encoder 76 may be communicatively coupled to the controller 52 configured to control the rotation and line scanning of the 2D line scanners 62 to obtain the 3D image or data of the interior surface 64 of the drilling riser pipe 36.

The various components of the scanning device 48 as discussed above may be included into an integrated package. For example, the scanning device 48 may include a mounting plate 78. The shaft 72 may be mounted onto, screwed to, glued onto, or otherwise coupled to the mounting plate 78. All or a part of various other components of the scanning device 48, including the 2D line scanners 62, the motor 74, and the rotary encoder 76, may be coupled to the shaft 72 or coupled to the mounting plate 78 directly. In some embodiments, the scanning device 48 may also include an outer shell substantially enclosing the various components of the scanning device 48. The outer shell may provide protection of the scanning device 48 from environment (e.g., drilling mud) within the bore 50 of the drilling riser pipe 36. In order to be deployable within the bore 50 of the drilling riser pipe 36, the scanning device 48 may have a diameter 86 along the radial axis 58 that is smaller than a diameter 88 along the radial axis 58 of the bore 50 of the drilling riser pipe 36. Likewise, in some embodiments, the diameter 86 of the scanning device 48 may be smaller than a diameter of a bore of various other tubular structures (e.g., other components of the riser equipment 18 such as the LMRP 40, components of the stack equipment 20 such as the one or more BOPs 42, and components of the wellhead 22) of the hydrocarbon extraction system 10 such that the scanning device may be deployable within the bore of the various other tubular structures for inspection of interior surfaces thereof.

As illustrated in FIG. 2, the scanning device 48 of the inspection system 12 may be suspended by a wireline or cable 80 positioned on a wireline spool 82. The wireline spool 82 may be communicatively coupled the controller 52 such that the controller 52 may control operations of the wireline spool 82. For example, the controller 52 may control the wireline spool 82 to extend the wireline 80 to lower (e.g., along the axial axis 56) the scanning device 48 within the core 50 of the drilling riser pipe 36, or to retract the wireline 80 to raise (e.g., along the axial axis 56) the scanning device 48 within the core 50 of the drilling riser pipe 36. The depth (e.g., along the axial axis 56) of the scanning device 48 within the core 50 of the drilling riser pipe 36 may be determined by the controller 52 based at least on the length of the wireline 80 that is extended or retracted and a reference position of the scanning device (e.g., the proximal end of the drilling riser pipe 36). In some embodiments, one or more linear encoders may be coupled to the wireline 80 and/or the scanning device 48 for determining or monitoring the depth (e.g., along the axial axis 56) of the scanning device 48 within the core 50 of the drilling riser pipe 36.

The inspection system 12 may also include the umbilical cable 54 coupling the scanning device 48 and the controller 52, for example, via an umbilical cable spool 84. The umbilical cable 54 is configured to transmit data between the controller 52 and the scanning device 48. In certain embodiments, the umbilical cable 54 may include fiber optics. For example, 2D and/or 3D images obtained by the scanning device 48 may be transmitted via the umbilical cable 54 from the scanning device 48 to the controller 52, where the images may be processed and analyzed. Data regarding angular positions of the line scanners 62 obtained by the rotary encoder 76 may also be transmitted from the scanning device 48 to the controller 52 via the umbilical cable 54. Control signals may be transmitted from the controller 52 to the scanning device 48 via the umbilical cable 54 to control operations of the various components of the scanning device 48, such as the rotation of scanning device 48 and data or image collection by the line scanners 62. The umbilical cable 54 may also be configured to transmit power from the controller 52 to the scanning device 48. For example, the controller 52 may be coupled to a separate or integrated power source (e.g., an electrical outlet, a battery, or a generator) for providing power to various components of the scanning device, such as the motor 74 and the line scanners 62.

Similarly, the controller 52 may control the umbilical cable spool 84 to extend or retract the umbilical cable 54. For example, the controller 52 may control the wireline spool 82 and the umbilical cable to operate in a concerted manner, for example, by extending or retracting the wireline 80 and the umbilical cable 54 with the same speed. In some embodiments, one or more linear encoders may be coupled to the umbilical cable 54 in addition to, or alternatively to, the wireline 80 for determining or monitoring the depth (e.g., along the axial axis 56) of the scanning device 48 within the core 50 of the drilling riser pipe 36. In certain embodiments, the umbilical cable 54 and the wireline 80 may be integrated together (e.g., joined as one strand, or a single cable performing functions of both the umbilical cable 54 and the wireline 80) extended or retracted by one spool (e.g., the wireline spool 82 or the umbilical cable spool 84).

Figure 3:
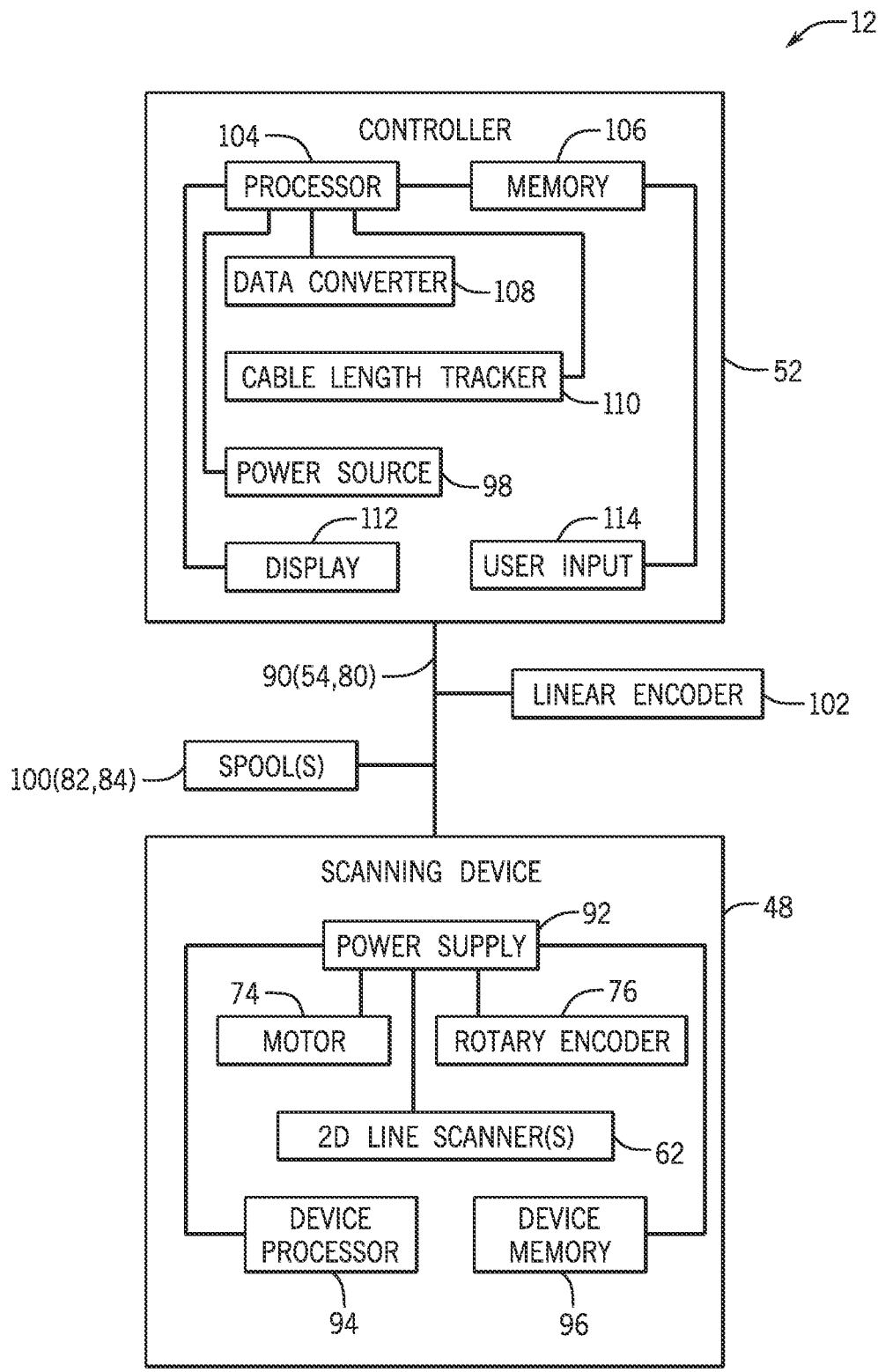
FIG. 3 is a block diagram of an embodiment of the components of the inspection system of FIG. 1, in accordance with the present the disclosure.

FIG. 3 is a block diagram of an embodiment of the inspection system 12 of FIG. 1. The inspection system 12 may include the scanning device 48, the controller 52, and one or more cable lines 90 (e.g., the umbilical cable 54, the wireline 80) coupling the scanning device 48 and the controller 52. As discussed above, the scanning device 48 may be disposed within any suitable tubular structures of the hydrocarbon extraction system 10 for inspecting interior surfaces thereof by using 2D and/or 3D line scanning.

The scanning device 48 may include various components, such as one or more 2D line scanners 62, the motor 74, the rotary encoder 76, a power supply 92, a device processor 94, and/or a device memory 96. The power supply 92 may include any suitable power source for providing electrical power to various components of the scanning device. As noted above, the power supply 92 may be a standalone battery integrated with the scanning device 48 or may be coupled to a remote power source (e.g., a power source 98) via the one or more cable lines 90 (e.g., the umbilical cable 54). The one or more 2D line scanners 62 may line scan the interior surface 64 of the drilling riser pipe 36 and obtain 2D and/or 3D images or data of the interior surface 64. The obtained images or data may be processed by the device processor 94. For example, the device processor 94 may perform analog to digital (A/D) conversions, digital to analog (D/A) conversions, electrical to optical (E/O) conversions, optical to electrical (O/E) conversions, data compressions, and/or data encodings. The device memory 96 may store one or more instructions executable by the device processor 94 for processing the obtained images or data. The device memory 96 may also store the processed and/or unprocessed images or data that may be transmitted via the one or more cable lines 90 (e.g., the umbilical cable 54) to the controller 52 for further processing and analysis. In some embodiments, the scanning device 48 does not include the device processor 94 or the device memory 96, and the obtained images or data may be directly transmitted from the one or more 2D line scanners 62 to the controller 52.

The one or more cable lines 90 (e.g., the umbilical cable 54, the wireline 80) couple the scanning device 48 and the controller 12. The one or more cable lines 90 may be positioned onto one or more spools 100 (e.g., the umbilical cable spool 84, the wireline spool 82) configured to lower or raise the scanning device 48 within the drilling riser pipe 36 by extending or retracting the one or more cable lines 90. The controller 12 may determine the depth of the scanning device 48 based at least on the extended or retracted length of the one or more cable lines 90. Additionally, or alternatively, one or more linear encoders 102 may be coupled to the one or more cable lines 90 to facilitate determining the depth of the scanning device 48 within the drilling riser pipe 36.

The controller may also include various components, such as the power source 98, a processor 104, a memory 106, a data converter 108, a cable length tracker 110, a display 112, and/or a user input 114. The power source 98 may be coupled to the power supply 92 to provide electric power to the scanning device 48. The power source may also provide electric power to the controller 52 and other components of the inspection system 12, such as the one or more spools 100 (e.g., the umbilical cable spool 84, the wireline spool 82) and the one or more linear encoders 102. In some embodiments, the power source 98 may be a separate unit from the controller 52.

The controller 52 may include a distributed control system (DCS) or any computer-based workstation that is fully or partially automated. For example, the controller 52 may be any device employing a general purpose or an application-specific processor (e.g., the processor 104), both of which may generally include memory circuitry (e.g., the memory 106) for storing instructions related to data processing and transmission, for example. The processor 104 may include one or more processing devices, and the memory 106 may include one or more tangible, non-transitory, machine-readable media collectively storing instructions executable by the processor 104 to perform the methods and control actions described herein.

Such machine-readable media can be any available media other than signals that can be accessed by the processor 106 or by any general purpose or special purpose computer or other machine with a processor. By way of example, such machine-readable media can include RAM, ROM, EPROM, EEPROM, CD-ROM, or other optical disk storage, magnetic disk storage or other magnetic storage devices, or any other medium which can be used to carry or store desired program code in the form of machine-executable instructions or data structures and which can be accessed by the processor 106 or by any general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions includes, for example, instructions and data which cause the processor or any general purpose computer, special purpose computer, or special purpose processing machine to perform a certain function or group of functions.

In some embodiments, the cable length tracker 110 is included in the controller 52 to control the operations (e.g., extension or retraction) of the one or more cable lines 90 (e.g., the umbilical cable 54, the wireline 80) and to track or monitor the extended or retracted cable length for determining the depth of the scanning device 48 when deployed within the drilling riser pipe 36. In other embodiments, the controller 52 may not include the cable length tracker 110, and the processor 104 coupled with the memory 106 may perform the tracking function of the cable length tracker 110.

The controller 52 may also include a data converter 108. The 2D/3D line scan images or data obtained by the one or more 2D line scanners 62 may be directly transmitted to the data converter 108 via the one or more cable lines 90. The data converter 108 may perform analog to digital (A/D) conversions, digital to analog (D/A) conversions, electrical to optical (E/O) conversions, optical to electrical (O/E) conversions, data compressions, and/or data encodings to the transmitted images or data and then transmit to the processor 104 for further procession and analysis.

The memory 106 may store any suitable instructions, programs, or algorithms, executable by the processor 104, for processing and analyzing the obtained 2D and/or 3D line scan images and/or any relevant data (e.g., the data related to the angular positions of the line scanners 62 provided by the rotary encoder 76) for determining structural integrity (e.g., for corrosion of interior, degrading of welding, or loosening of connectors) of the drilling riser pipe 36. For example, the algorithms may include an automatic defect recognition (ADR), by which the processor 104 may compare images or data of same spots (e.g., surface spots on the interior surface 64 of the drilling riser pipe 36) at various times to determine whether or not the spots have undergone certain chemical or physical changes, such as formation of cavities due to corrosion or formation of buildups due to deposits from the drilling mud or other contaminates.

The memory 106 may also store any suitable instructions, programs, or algorithms, executable by the processor 104, for controlling various components of the scanning device 48. For example, the instructions may include directing the one or more line scanners 62 to rotate in certain directions, with certain speeds, and/or line scan a portion of a circumference of the interior surface 64 of the drilling riser pipe 36 with certain periods of time before moving to another angular position. As another example, the instructions may include directing the one or more line scanners 62 to operate in parallel or in alternating manners.

The controller 52 may further include the display 112 for displaying processed or unprocessed images or data or any other relevant information, such as the depth of the scanning device, the length of the extended or retracted cables 90. The inspection system 12 may also include various sensors, such as temperature sensors, pressure sensors, positions sensors, proximity sensors, coupled to one or more components of the inspection system 12 (e.g., the scanning device 48). The feedback from the various sensors may be used by the controller 54 to monitor operations and/or operating environment of the scanning device 48, and in turn to adjust the operations of the scanning device 48. The feedback may also be provided to a user via the display 112. In some embodiments, the user may via the user input 114 control the operations of the inspections system 12, for example, the depth of the scanning device 48 within the drilling riser pipe 36. The user may also via the user input 114 direct the controller to process and analyze the obtained 2D and/or 3D images or data. The user input 114 may include a keyboard, a mouse, a voice commanding device, a touch screen, a writing pad, or any combination thereof.

Figure 4:
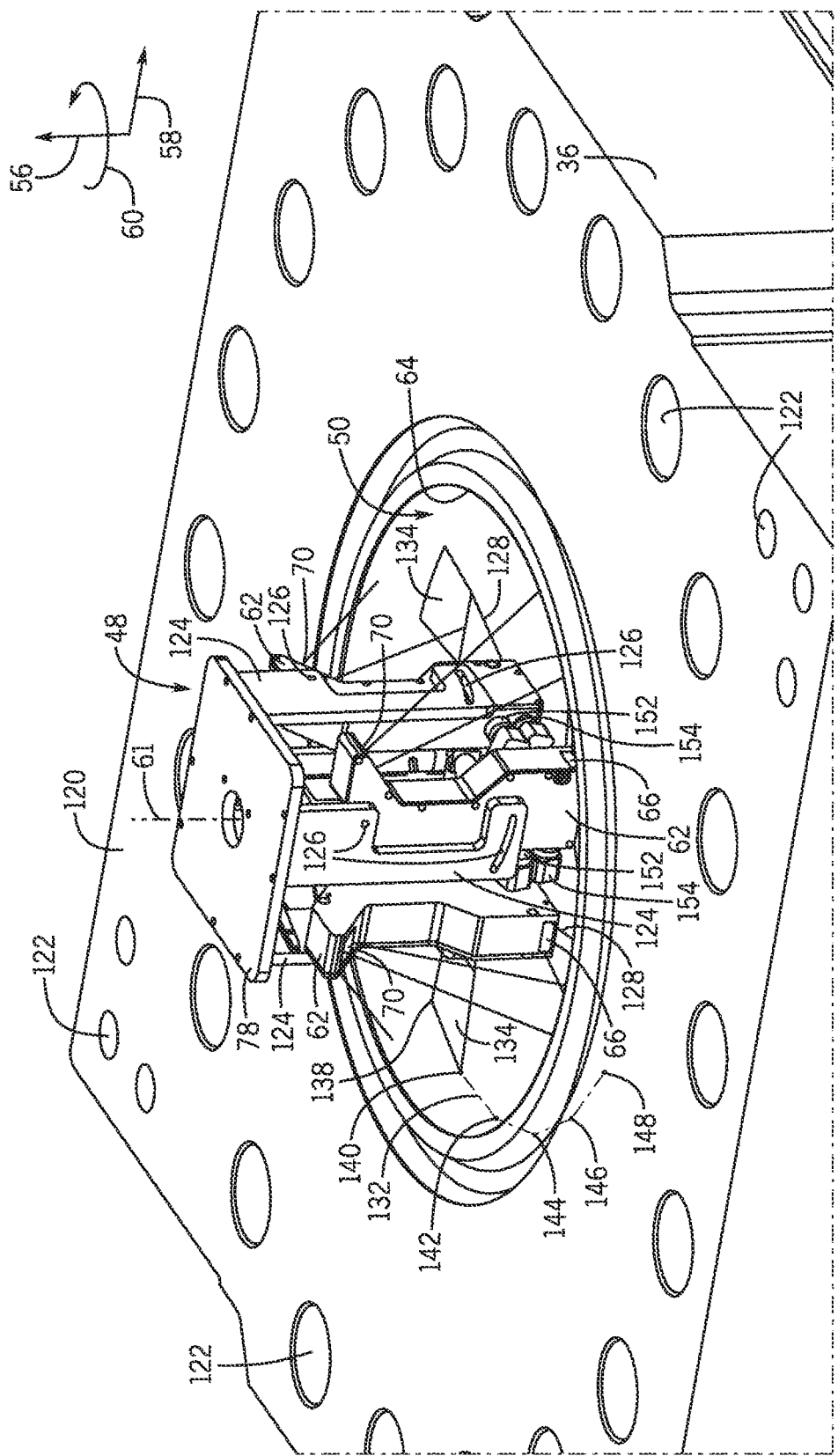
FIG. 4 is a perspective view of an embodiment of a scanning device of the inspection system of FIG. 1, in accordance with the present the disclosure.
Figure 5:
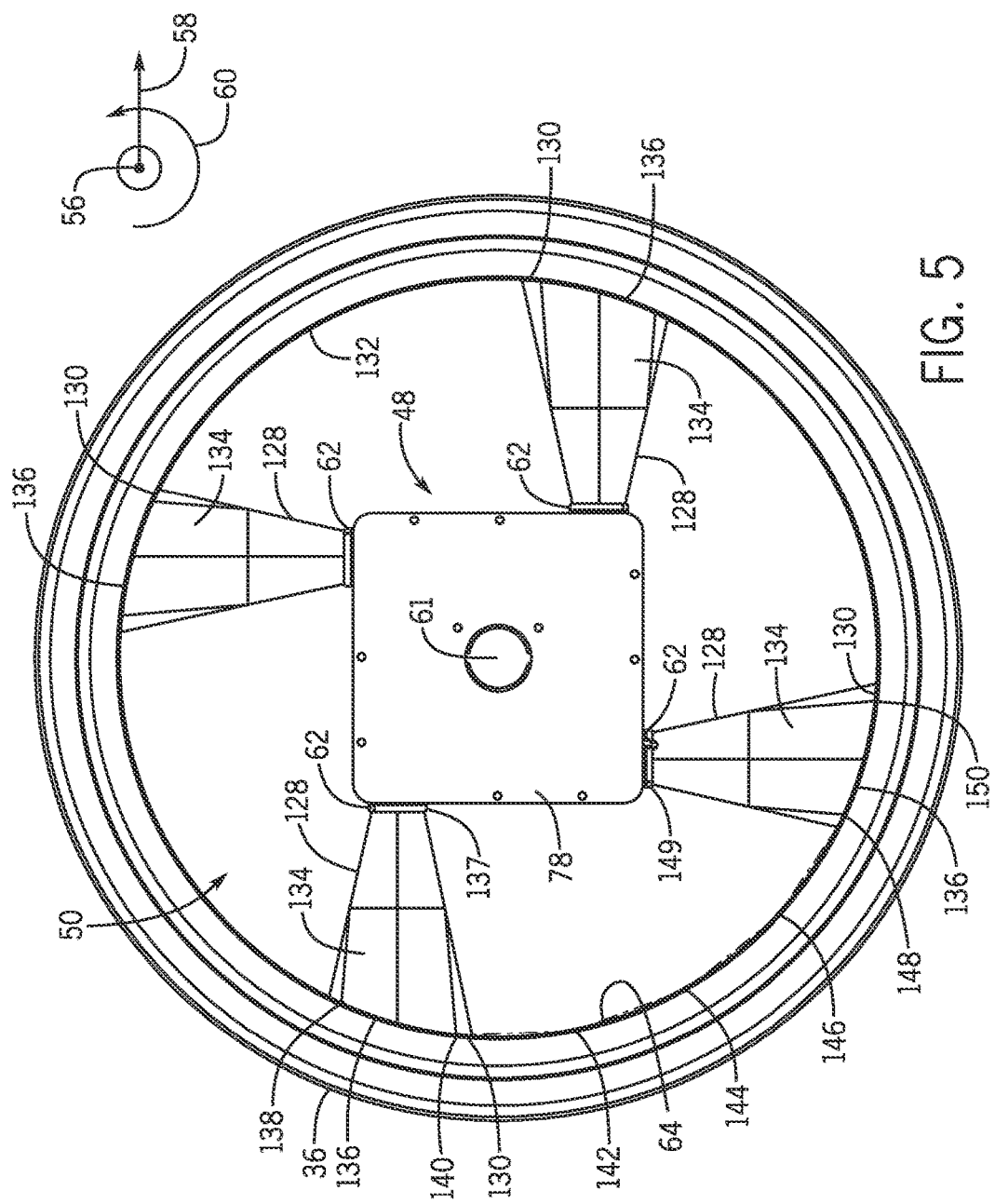
FIG. 5 is a top view of the embodiment of the scanning device of FIG. 4, in accordance with the present the disclosure.
Figure 6:
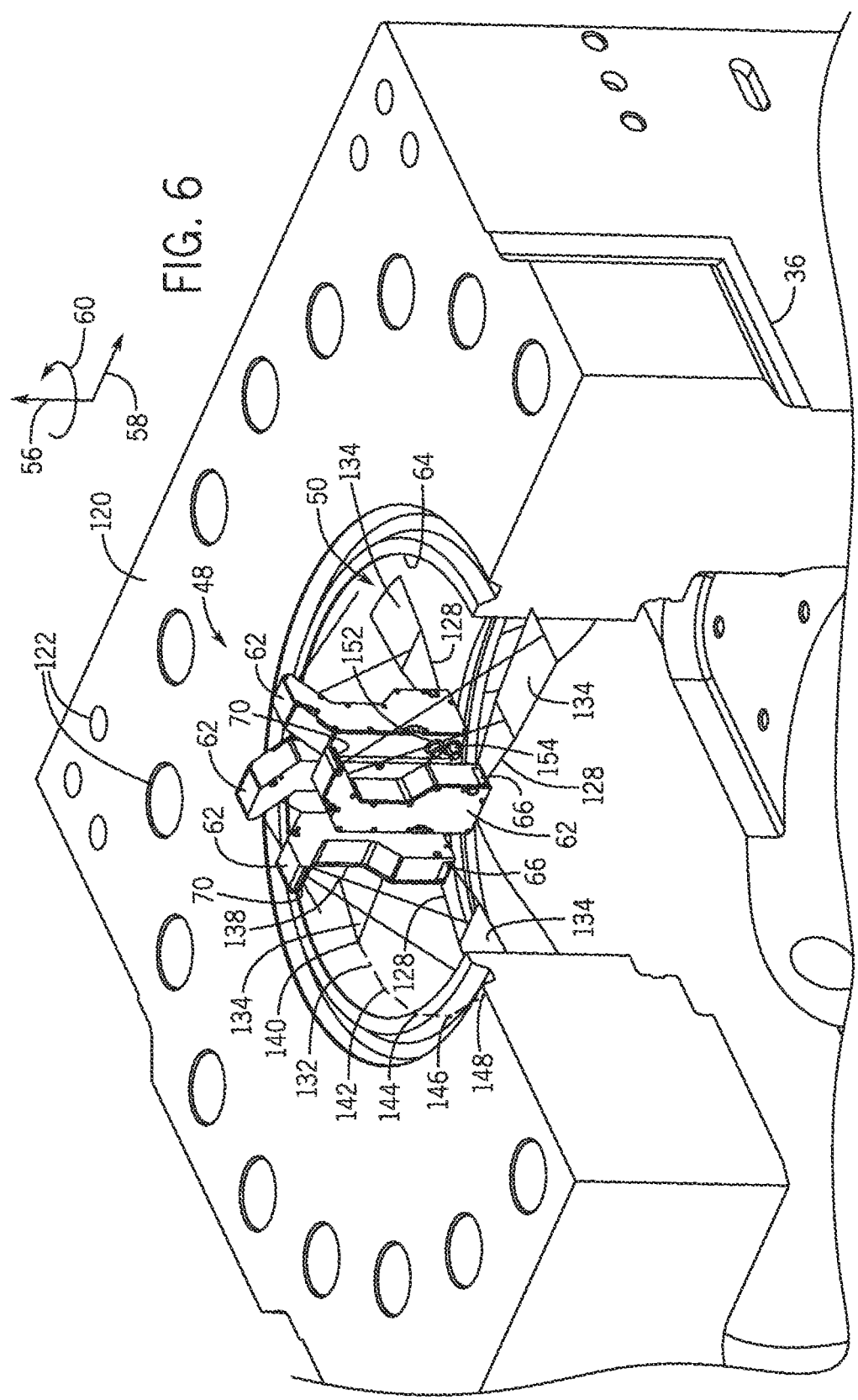
FIG. 6 is an exposed view of the embodiment of the scanning device of FIG. 4, in accordance with the present the disclosure.

FIGS. 4-6 illustrate an embodiment of the scanning device 48 disposed within the bore 50 of the drilling riser pipe 36. FIG. 4 is a perspective view of the embodiment of the scanning device 48. FIG. 5 is a top view of the embodiment of the scanning device 48. FIG. 6 is a somewhat exposed view of the embodiment of the scanning device 48 with some of the components of the scanning device 48 removed for a better view of the line scanners 62. For illustrative purposes, FIGS. 4 and 6 show a cross section 120 of the drilling riser pipe 36. The drilling riser pipe 36 may also include multiple auxiliary conduits or lines 122 for various other purposes, such as choke, kill, and hydraulic boost purposes. As illustrated, the scanning device 48 is deployed substantially about the center of the bore 50, and the longitudinal axis 61 of the scanning device 48 is generally parallel to the axial axis 56 and runs generally through the center of the bore 50 of the drilling riser pipe 36.

The scanning device 48 includes the mounting plate 78 at its proximal end. Different from the embodiment as illustrated in FIG. 2, the embodiment of the scanning device 48 as illustrated in FIGS. 4 and 5 does not include the shaft 72. Instead, the illustrated embodiment includes four side plates or poles 124 coupled to the mounting plate 78 with a 2D line scanner 62 coupled to each of the four side plates 124, respectively. For example, each of the four 2D line scanners 62 may be fastened to the respective side plate 124 with one or more screws 126. As noted above, although the illustrated embodiment includes four 2D line scanners 62, the scanning devices may include any number of 2D line scanners 62, such as 1, 2, 3, 4, 5, 6, 7, 8, 9, 10, or more.

Each of the 2D line scanners 62 may include the emitter 66 and the camera 70 for line scanning The emitter 66 may be positioned at the distal end (e.g., closer to the sea bottom 24) of the 2D line scanner 62, and the camera 70 may be positioned at the proximal end (e.g., closer to the floating vessel 26) of the 2D line scanner 62. However, it should be noted that the emitter 66 and the camera 70 may be positioned in an opposite configuration (e.g., with the emitter 66 at the proximal end and the camera 70 at the distal end) or any other suitable configurations. In addition, in the illustrated embodiment, each of the 2D line scanners 62 is disposed in a substantially vertical position (e.g., with the emitter 66 and the camera 70 along the axial axis 56). However, it should be noted that each of the 2D line scanners 62 may be disposed in a substantially horizontal position (e.g., with the emitter 66 and the camera 70 on the plane defined by the radial axis 58 and the circumferential axis 60) or any other suitable positions.

As illustrated, each of the emitters 66 may emit a laser beam 128 travelling substantially perpendicular to the interior surface 64 (e.g., perpendicular to the longitudinal axis 61). The laser beam 128 may project a thin laser line 130 onto the interior surface 64 with the thin laser line 130 covering a portion of a circumference 132 (e.g., on the plane defined by the radial axis 58 and the circumferential axis 60) of the interior surface 64. In the illustrated embodiment, the four 2D line scanners are positioned with respect to one another such that all of the projected laser lines 130 substantially are on the same circumference 132. That is, all of the projected laser lines 130 are substantially on the same plane defined by the radial axis 58 and the circumferential axis 60, which is perpendicular to the longitudinal axis 61 of the scanning device 48. Consequently, when the scanning device 48 (e.g., the four 2D line scanners 62) rotates with respect to the longitudinal axis 61, the whole circumference 132 may be covered by the one or more projected laser lines 130.

Each of the cameras 70 may take images of the respective projected laser lines 130. As illustrated, each of the cameras 70 may be configured with respect to the respective emitter 66 such that the respective projected laser line 130 is within a field of view of the respective camera 70. For example, the field of view of each of the cameras 70 may be projected to intersect with the respective laser beam 128, resulting in an overlapping area 134. Each of the overlapping areas 134 may intersect with the interior wall 64, resulting in an imaging line 136 covering a portion of the circumference 132. Any object that is within each of the overlapping areas 134, including the respective imaging line 136, may be imaged on the field of view of the respective camera 70. Accordingly, the portion of the circumference 132 that is covered by the imaging lines 136, as well as surface features (e.g., protrusions, or cavities) associated with (e.g., radially below or above) such portion may be imaged by the cameras 70. In the illustrated embodiment, each of the imaging lines 136 is shorter than the respective projected laser line 130. However, it should be noted that each of the imaging lines 136 may be approximately equal to the respective projected laser line 130 depending at least on the configuration of the respective camera 70 (e.g., the field of view) and laser beam profile of the respective emitter 62.

As illustrated, each of the four imaging lines 136 covers approximately 1/20 of the circumference 132 in one sweep (e.g., rotation by a certain angle with respect to the longitudinal axis 61). As such, the illustrated scanning device 48 that includes four imaging line scanners 62 may line scan approximately the whole circumference 132 in five sweeps. For example, a first line scanner 137 of the four line scanners 62 covers the circumference 132 approximately between a first point 138 and a second point 140 on the circumference 132, as shown, after a first sweep. The scanning device 48 may then rotate with respect to the longitudinal axis 61 by a certain degree (e.g., a second sweep) such that after the second sweep, the first line scanner 137 covers the circumference 132 approximately between the second point 140 and a third point 142 on the circumference 132. Likewise, the scanning device 48 may then rotate with respect to the longitudinal axis 61 by approximately the same degree (e.g., a third sweep) such that after the third sweep, the first line scanner 137 covers the circumference 132 approximately between the third point 142 and a fourth point 144 on the circumference 132. The scanning device 48 may then rotate with respect to the longitudinal axis 61 by approximately the same degree (e.g., a fourth sweep) such that after the fourth sweep, the first line scanner 137 covers the circumference 132 approximately between the fourth point 144 and a fifth point 146 on the circumference 132. The scanning device 48 may then rotate with respect to the longitudinal axis 61 by approximately the same degree (e.g., a fifth sweep) such that after the fifth sweep, the first line scanner 137 covers the circumference 132 approximately between the fifth point 146 and a sixth point 148 on the circumference 132. Because a second line scanner 149 covers the circumference 132 approximately between the sixth point 148 and a seventh point 150 on the circumference 132, as shown, after the first sweep, all four line scanners 62 may cover approximately the whole circumference 132 after the five sweeps.

It should be noted that the embodiment as illustrated in FIGS. 4 and 5 are meant to be a non-limiting example. As noted above, the scanning device 48 may include any number of line scanners 62. Each line scanner may be configured to cover a suitable portion of the circumference 132, and the scanning device may cover the whole circumference 132 in any suitable number of sweeps. For example, the scanning device 48 may include one line scanner 62 that may be line scan (e.g., cover) approximately 60 degrees with respect to the longitudinal axis 61. As such, the scanning device may rotate with respect to the longitudinal axis 61 and line scan the whole circumference 132 (e.g., 360 degrees) in approximately 6 sweeps.

The circumference 132, on the plane defined by the radial axis 58 and the circumferential axis 60, corresponds to a specific depth of the scanning device 48 within the drilling riser pipe 36. As the whole circumference 132 is line scanned, a 2D image may be generated. As noted above, the scanning device 48 may be controlled to move upward or downward along the axial axis 56. Accordingly, various circumferences, corresponding to various different depths (e.g., along the axial axis 56), of the interior surface 64 may be line scanned. Consequently, a 3D image may be generated based on integrating various 2D images at the various depths and/or data related to the angular positions of the line scanners 62 provided by the rotary encoder 76.

As shown in FIGS. 4 and 6, each of the line scanners 62 includes other components, such as a power port 152 and a data port 154. The power port 152 may be used for connecting a power cable to the power supply 92 of the scanning device 48 or the power source 98 of the controller 52 to provide electric power to the respective line scanner 62. The data port 154 may be used for connecting a data line to the device processor 94 and/or the device memory 96, in addition or alternatively, to the processor 104, memory 106, and/or the data converter 108 of the controller 52, for transmitting data (e.g., images and control signals) between the respective line scanner 62 and the scanning device 48 and/or the controller 52.

Figure 7:
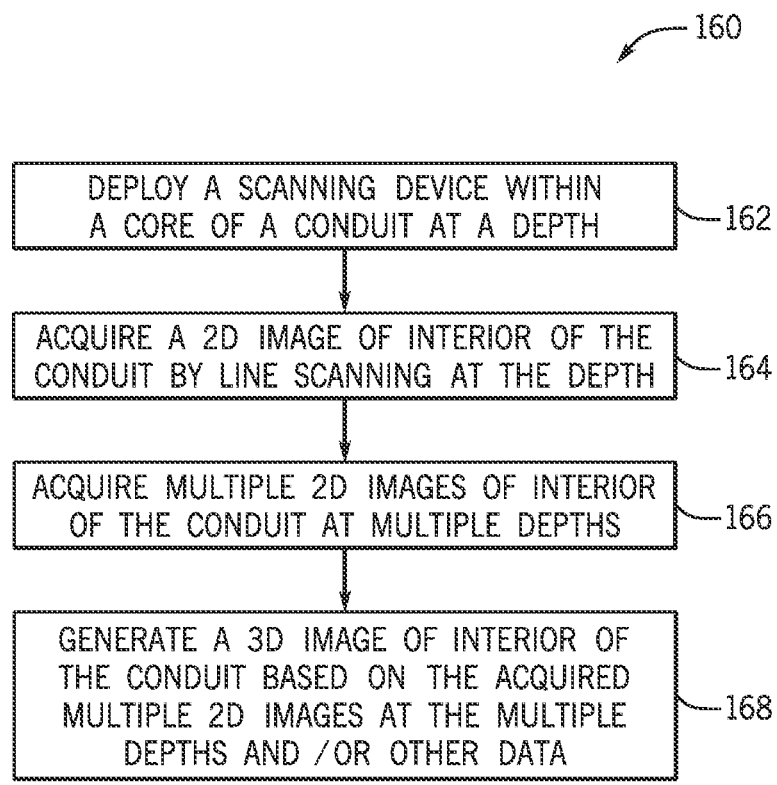
FIG. 7 is a flow diagram of a method for inspecting a tubular structure of the hydrocarbon extraction system of FIG. 1, in accordance with the present disclosure.

FIG. 7 is a flow diagram of a method 160 for inspecting an interior surface of a tubular structure (e.g., a conduit) of the hydrocarbon extraction system 10 using the inspection system 12, in accordance with the present disclosure. For example, the method 160 may be used for inspecting the interior surface 64 of the drilling riser pipe 36, as discussed above. The inspection system 12 may include the scanning device 48, the controller 52, and one or more cable lines 90 (e.g., the umbilical cable 54, the wireline 80) coupling the scanning device 48 and the controller 52

The method 160 may start with deploying the scanning device 48 within a core of a conduit at a depth (block 162). The scanning device 48 may be deployed to the conduit without disassembling the components of the conduit or disassembling the conduit from other adjoining equipment. As noted above, the conduit may be the drilling riser pipe 36 that may include one or more riser pipe sections. The scanning device 48 may be deployed within the drilling riser pipe 36 when the drilling riser pipe 36 is deployed offshore for drilling, thereby eliminating the disassembly, transportation, and reassembly of the components of the drilling riser pipe 36. The scanning device 48 may be deployed to the depth by utilizing the one or more cable lines 90. The depth may be monitored or determined by the controller 52.

At the depth, the controller 52 may control the scanning device 48 to acquire a 2D image of a circumference of the interior wall of the conduit by using laser line scanning (block 164). The scanning device 48 may include one or more 2D laser line scanners 62. At one sweep, the scanning device 48 may line scan a portion of the circumference of the interior wall. As such, the whole circumference of the interior wall may be line scanned by the one or more 2D laser line scanners 62 in multiple sweeps. The 2D image may reflect surface features along the circumference of the interior wall of the conduit. The acquired 2D image may be transmitted from the scanning device 48 to the controller 52 via the one or more cable lines 90.

The controller 52 may then control the scanning device 48 to move to one or more other depths within the conduit. For example, the controller 52 may control the depths of the scanning device 48 by extending or retracting the one or more cable lines 90. At each of the other depths, the scanning device 48 may similarly acquire a 2D image of another circumference of the interior wall of the conduit (block 166). The acquired 2D image(s) may likewise be transmitted from the scanning device 48 to the controller 52 via the one or more cable lines 90.

After acquiring the multiple 2D images corresponding to the multiple depths of the conduit, the controller may generate a 3D image of the interior of the conduit based on the acquired multiple 2D images and/or other data (e.g., the data related to the angular positions of the line scanners 62 provided by the rotary encoder 76) (block 168). The generated 3D image may reflect surface features of the interior of the conduit. The controller 12 may then process and analyze the generated 3D images for determining or detecting structural integrity (e.g., inspection of corrosion of interior, degrading of welding, or loosening of connectors) of the interior of the conduit.

This written description uses examples to disclose the embodiments, including the best mode, and also to enable any person skilled in the art to practice the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system, comprising:
a vessel floating on a body of water;
at least one conduit extending from the vessel to below the body of water; and
a scanning device disposed within the at least one conduit, wherein the scanning device comprises a mounting plate, a shaft having an end coupled to the mounting plate, a plurality of two-dimensional (2D) line scanners disposed circumferentially about the shaft, and a rotary encoder coupled to the plurality of 2D line scanners, wherein the scanning device is configured to generate three-dimensional (3D) image data of a surface of the at least one conduit or at least one component disposed within the at least one conduit, and wherein each 2D line scanner of the plurality of 2D line scanners comprises an emitter disposed adjacent a first end of the respective 2D line scanner and a camera adjacent both the end and a second end of the respective 2D line scanner opposite the first end, each respective emitter of the plurality of 2D line scanners is configured to initially emit a beam of light perpendicular to respective longitudinal axes of the at least one conduit and the scanning device to intersect with the surface to produce an intersection line, and each respective camera of the plurality of 2D line scanners to is configured image a respective intersection line to produce two-dimensional (2D) image data, and wherein the rotary encoder is configured to monitor an angular position of the plurality of 2D line scanners relative to the longitudinal axis of the scanning device.

2. The system of claim 1, wherein the scanning device is configured to be rotated 360 degrees about the longitudinal axis of the scanning device to acquire data of the surface of the at least one conduit or the at least one component disposed within the at least one conduit.

3. The system of claim 1, wherein the scanning device comprises a motor coupled to the plurality of 2D line scanners and configured to drive the plurality of 2D line scanners to rotate relative to the longitudinal axis of the scanning device.

4. The system of claim 1, comprising a wireline coupled to the scanning device and positioned on a wireline spool, wherein the wireline spool is configured to extend or retract the wireline to change a depth of the scanning device within the at least one conduit.

5. The system of claim 4, wherein the wireline spool is configured to be controlled to extend or retract the wireline manually, automatically, or a combination thereof.

6. The system of claim 1, wherein the at least one conduit comprises a drilling riser pipe, a lower marine riser package (LMRP), a blowout preventer (BOP), a wellhead, or any combination thereof.

7. A system, comprising:
a scanning device configured to be disposed within a conduit, wherein the scanning device comprises a mounting plate, a shaft having an end coupled to the mounting plate, a plurality of two-dimensional (2D) line scanners disposed circumferentially about the shaft, and a rotary encoder coupled to the plurality of 2D line scanners, wherein the scanning device is configured to generate two-dimensional (2D) image data of a first surface of the conduit, a second surface of a component disposed within the conduit, or a third surface of an object above the conduit, and wherein each 2D line scanner of the plurality of 2D line scanners comprises an emitter disposed adjacent a first end of the respective 2D line scanner and a camera adjacent both the end and a second end of the respective 2D line scanner opposite the first end, each respective emitter of the plurality of 2D line scanners is configured to initially emit a beam of light perpendicular to respective longitudinal axes of the at least one conduit and the scanning device to intersect with the first surface, the second surface, or the third surface to produce an intersection line, and each respective camera of the plurality of 2D line scanners to image a respective intersection line is configured to produce 2D image data; and
a controller coupled to the scanning device and configured to acquire the 2D image data from the scanning device and to generate three-dimensional (3D) image data from at least the acquired 2D image data, wherein the rotary encoder is communicatively coupled to the controller and is configured to acquire data indicative of an angular position of the plurality of 2D line scanners relative to the longitudinal axis of the scanning device, and to transmit the data to the controller.

8. The system of claim 7, wherein the controller is configured to rotate the scanning device 360 degrees about the longitudinal axis of the scanning device to acquire data of the first, second, or third surfaces.

9. The system of claim 7, wherein the scanning device comprises a motor coupled to the plurality of 2D line scanners and communicatively coupled to the controller, and the controller is configured to control the motor to drive the plurality of 2D line scanners to rotate relative to the longitudinal axis of the scanning device.

10. The system of claim 7, comprising a wireline coupled to the scanning device and positioned on a wireline spool, wherein the controller is configured to control the wireline spool to extend or retract the wireline to position the scanning device at a specific depth within the conduit.

11. The system of claim 7, comprising an umbilical cable coupling the scanning device and the controller, wherein the umbilical cable is configured to transmit the 2D image data from the scanning device to the controller, and to transmit control signals, power, or a combination thereof, from the controller to the scanning device.

12. A method comprising:
disposing a scanning device within a conduit, wherein the scanning device comprises a mounting plate, a shaft having an end coupled to the mounting plate, a plurality of two-dimensional (2D) line scanners circumferentially disposed about the shaft, and a rotary encoder coupled to the plurality of 2D line scanners, wherein each 2D line scanner of the plurality of 2D line scanners comprises an emitter disposed adjacent a first end of the respective 2D line scanner and a camera adjacent both the end and a second end of the respective 2D line scanner opposite the first end;
emitting from each respective emitter of the plurality of 2D line scanners a respective beam of light perpendicular to respective longitudinal axes of the at least one conduit and the scanning device to intersect with a first surface of the conduit, a second surface of a component within the conduit, or a third surface of an object above the conduit using the scanning device to produce an intersection line;
rotating the plurality of 2D line scanners relative to the longitudinal axis of the scanning device based on data indicative of an angular position of the plurality of 2D line scanners relative to the longitudinal axis of the scanning device, wherein the data is acquired by the rotary encoder;
acquiring two-dimensional (2D) image data of the first surface, the second surface, or the third surface by imaging, via each respective camera of the plurality of 2D line scanners, a respective intersection line; and
generating three-dimensional (3D) image data from at least the 2D image data.

13. The method of claim 12, wherein acquiring 2D image data comprises rotating the plurality of 2D line scanners 360 degrees about the longitudinal axis of the scanning device to acquire the 2D image data of the first, second, or third surfaces.

14. The method of claim 12, comprising:
acquiring data indicative of multiple depths of the scanning device within the conduit;
wherein acquiring the 2D image data of the first surface of the conduit or the second surface of the component within the conduit comprises acquiring the 2D image data of the first surface of the conduit or the second surface of the component disposed within the conduit at the multiple depths; and
wherein generating the 3D image data from at least the acquired 2D image data comprises generating the 3D image data based on the acquired 2D image data and the data indicative of multiple depths of the scanning device within the conduit.

* * * * *